United States Patent
Evans et al.

(10) Patent No.: US 10,238,548 B2
(45) Date of Patent: Mar. 26, 2019

(54) WATER-RESISTANT ORTHOPEDIC UNDERCAST SLEEVE PRODUCT

(75) Inventors: John C. Evans, NR Rochdale (GB); Shitij Chabba, Charlotte, NC (US); Martin O'Hara, Charlotte, NC (US)

(73) Assignee: BSN MEDICAL, INC., Charlotte, NC (US)

( * ) Notice: Subject to any disclaimer, the term of this patent is extended or adjusted under 35 U.S.C. 154(b) by 1700 days.

(21) Appl. No.: 11/995,552

(22) PCT Filed: Jul. 14, 2006

(86) PCT No.: PCT/US2006/027248
§ 371 (c)(1),
(2), (4) Date: Sep. 3, 2008

(87) PCT Pub. No.: WO2007/011664
PCT Pub. Date: Jan. 25, 2007

(65) Prior Publication Data
US 2009/0112138 A1    Apr. 30, 2009

Related U.S. Application Data

(60) Provisional application No. 60/699,077, filed on Jul. 14, 2005.

(51) Int. Cl.
*A61F 13/06* (2006.01)
*A61F 13/04* (2006.01)
(Continued)

(52) U.S. Cl.
CPC .......... *A61F 13/041* (2013.01); *A61F 15/008* (2013.01); *A61F 2013/00093* (2013.01)

(58) Field of Classification Search
CPC .................. A61F 13/041; A61F 15/008; A61F 2013/00093; A61F 2013/00097; A61F 2013/00238
(Continued)

(56) References Cited

U.S. PATENT DOCUMENTS 3,902,484 A  *  9/1975  Winters .................. 128/849
4,793,330 A    12/1988  Honeycutt et al.
(Continued)

FOREIGN PATENT DOCUMENTS

JP    A-2-126849    5/1990
JP    A-5148849    6/1993
(Continued)

OTHER PUBLICATIONS

Dec. 14, 2010 Office Action issued in Japanese Patent Application No. 2008-521617 (with translation).

*Primary Examiner* — Victoria J Hicks
(74) *Attorney, Agent, or Firm* — Shumaker, Loop & Kendrick, LLP.

(57) ABSTRACT

A water-resistant orthopedic undercast sleeve that includes a tubular sheet material formed of extruded filaments having water-resistant properties and a thickness sufficient to provide both cushioning and moisture transport in a single layer between a cast and a limb onto which the sleeve is applied. The water resistant properties are achieved by at least one process, including a water-resistant filler, finish or coating applied to the filaments during extrusion, applying a water resistant finish to the finish during extrusion, applying a water resistant finish to the filaments during a subsequent spinning process, or coating the filaments with a water-resistant finish in a separate process. Moisture egress channels are formed in the sheet material for transporting moisture away from the limb, longitudinally along the length of the sleeve, and out of the space between the sleeve and cast.

2 Claims, 3 Drawing Sheets

(51) Int. Cl.
*A61F 15/00* (2006.01)
*A61F 13/00* (2006.01)

(58) Field of Classification Search
USPC .................................. 128/892, 846
See application file for complete search history.

(56) References Cited

U.S. PATENT DOCUMENTS

| | | | |
|---|---|---|---|
| 4,829,993 A * | 5/1989 | Silvey ................................ | 602/9 |
| 5,916,184 A | 6/1999 | McKeel | |
| 6,981,955 B2 * | 1/2006 | Schultze et al. .................. | 602/3 |
| 7,682,994 B2 * | 3/2010 | Van Emden et al. ......... | 442/181 |
| 2002/0115369 A1 * | 8/2002 | Yokoyama et al. .......... | 442/308 |
| 2004/0193083 A1 * | 9/2004 | Evans et al. ..................... | 602/8 |
| 2005/0136758 A1 * | 6/2005 | Newton .................. | B29C 70/22 |
| | | | 442/43 |
| 2007/0281567 A1 * | 12/2007 | Baychar ................ | A41D 31/02 |
| | | | 442/181 |

FOREIGN PATENT DOCUMENTS

| | | |
|---|---|---|
| JP | A-9-510901 | 11/1997 |
| JP | A-2001-61883 | 3/2001 |
| JP | A2004-468 | 8/2004 |
| WO | WO 95/26698 A1 | 10/1995 |
| WO | 2005004765 A1 | 1/2005 |

* cited by examiner

WATER-RESISTANT ORTHOPEDIC UNDERCAST SLEEVE PRODUCT

TECHNICAL FIELD AND BACKGROUND OF THE INVENTION

The invention relates to a water-resistant undercast sleeve. In this application, the term "stockinette" is used to refer to prior art structures that are applied directly to the skin. In conventional casting practice, a stockinette is first applied to the injured limb to reside directly against the skin of the patient. The stockinette is usually formed of a thin circular-knit product that has sufficient stretch to allow it to fit onto the limb and closely conform to the varying shapes, contours and dimensions of the limb without wrinkles, overlaps or puckers that could cause discomfort or abrasion to the skin.

A padding is then applied over the stockinette onto the injured limb before the application of the cast tape. The padding provides a cushion and spacing between the skin and the cast tape, and protection to the bony prominences of the limb, and further aids in patient comfort. The stockinette and padding together form a system that collectively provides protection to the limb while the overlying cast tape provides the necessary support and rigidity to immobilize the limb during healing.

However, the conventional stockinette and padding system is not resistant to perspiration and/or moisture and when wet can give off odor and become uncomfortable to wear. This leads to a higher incidence of skin irritation and maceration, and in many instances may require removal and replacement of an otherwise medically effective cast. These factors have traditionally provided the majority of complaints regarding what is otherwise a medically-sound and cost-effective treatment regimen for bone fractures and other conditions requiring extended immobilization of a limb.

The invention described in this application discloses an undercast sleeve, which will replace both the conventional stockinette and padding. In addition to providing a satisfactory level of cushioning, this sleeve also repels water and dries quickly when wetted. The water-resistant sleeve of this invention is aimed at providing more freedom to the patient and help them carry out daily routine activities with much ease. Similar efforts have been conducted in the past to develop a water-resistant undercast sleeve, as described in U.S. Pat. No. 5,540,964 and WO2005/004765. However, none of the efforts have resulted in a successful working product.

The '964 patent discloses a sleeve constructed using hydrophilic fibers with an applied hydrophilic finish. The recited principle is to wick moisture away from the skin. However, the cast material itself is relatively impervious to both air and moisture transfer, so the wicking action moves the moisture into the overlying padding and cast material, where it accumulates in the padding and in the structure of the cast.

The WO '765 publication discloses a sleeve using microdenier fibers to wick moisture away from the skin, but this product has not proven effective for reasons similar to the '964 patent.

In contrast to these prior art attempts to solve the moisture-retention problem with hydrophilic products, applicant has discovered a means of utilizing hydrophobic materials to drain moisture away from the skin utilizing a combination of fabric mechanics and fiber technology.

SUMMARY OF THE INVENTION

Therefore, it is an object of the invention to provide a single product that replaces both a conventional stockinette and undercast padding system.

It is another object of the invention to provide a sleeve that resists moisture accumulation and retention.

It is another object of the invention to provide a sleeve that dries rapidly when wet.

It is another object of the invention to provide a sleeve that can be fabricated from a variety of materials.

It is another object of the invention to provide a sleeve that can be used with both plaster and synthetic casting materials.

These and other objects and advantages are achieved by providing a water-resistant orthopedic undercast sleeve, comprising: a tubular sheet material formed of extruded filaments having water-resistant properties and a thickness sufficient to provide both cushioning and moisture transport in a single layer between a cast and a limb onto which the sleeve is applied. The water-resistant properties result in a material selected from the group consisting of a water-resistant filler, finish or coating applied to the filaments during extrusion, a water-resistant finish applied to the filaments during extrusion, a water resistant finish applied to the filaments during a subsequent spinning process, or a water-resistant coating applied to the filaments with a water-resistant in a separate process. Moisture egress channels are formed in the sheet material for transporting moisture away from the limb, longitudinally along the length of the sleeve, and out of the space between the sleeve and cast. The sheet material has sufficient resistance to compression so as to maintain the moisture egress channels subsequent to application of a cast over the sheet material.

According to a preferred embodiment of the invention, the water-resistant finish coating comprises a wax, fluorochemical or nano-coating.

According to another preferred embodiment of the invention, the tubular sheet material comprises a tubular knitted fabric having separate, spaced-apart top and bottom layers joined by connectors selected from the group consisting of interconnecting yarns, stitches, glue joints or ultrasonic weld spots.

According to yet another embodiment of the invention, the tubular sheet material comprises a tubular non-woven fabric.

According to yet another embodiment of the invention the tubular sheet material comprises a tubular open cell foam.

According to yet another embodiment of the invention the tubular knitted fabric is formed in an elongate roll of sufficient length to permit multiple lengths suitable for application to a limb to be severed from the roll, as and when needed.

According to yet another embodiment of the invention, the tubular knitted fabric is provided in pre-cut lengths suitable for application to a limb of a predetermined size and length.

According to yet another embodiment of the invention, the tubular knitted fabric comprises low moisture regain hydrophobic fiber selected from the group consisting of polyester and polypropylene.

According to yet another embodiment of the invention the construction of the tubular knitted fabric is selected from the group consisting of a single knit rib construction and a double knit rib construction.

According to yet another embodiment of the invention, the tubular knitted fabric comprises a rib knit construction wherein the ribs extend longitudinally along the length of the sleeve.

According to yet another embodiment of the invention, the sleeve is knitted from a hydrophobic, low filament, multifilament yarn with a filament count of at least 10 and having a total denier of between 50 and 2000.

According to yet another embodiment of the invention, the sleeve is knitted from a hydrophobic, low filament, multifilament yarn with a filament count of at least 10 and having a total denier of between 500-1500.

According to yet another embodiment of the invention, the sleeve is a 2×2 rib-knit formed a hydrophobic, low filament, multifilament yarn with a filament count of at least 10 and having a total denier of between 50 and 2000.

According to yet another embodiment of the invention, a water-resistant orthopedic undercast sleeve is provided, comprising a tubular sheet material formed of extruded filaments having water-resistant properties and a thickness sufficient to provide both cushioning and moisture transport in a single layer between a cast and a limb onto which the sleeve is applied. The tubular sheet material comprises a tubular knitted fabric having separate, spaced-apart top and bottom layers joined by connectors selected from the group consisting of interconnecting yarns, stitches, glue joints or ultrasonic weld spots. The water-resistant properties are achieved by at least one process, comprising a water-resistant filler, finish or coating applied to the filaments during extrusion, or applying a water-resistant finish to the finish during extrusion, applying a water resistant finish to the filaments during a subsequent spinning process, or coating the filaments with a water-resistant finish in a separate process, wherein the water-resistant finish coating comprises a wax, fluorochemical or nano-coating. Moisture egress channels are formed in the sheet material for transporting moisture away from the limb, longitudinally along the length of the sleeve, and out of the space between the sleeve and cast. The sheet material ha sufficient resistance to compression so as to maintain the moisture egress channels subsequent to application of a cast over the sheet material.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
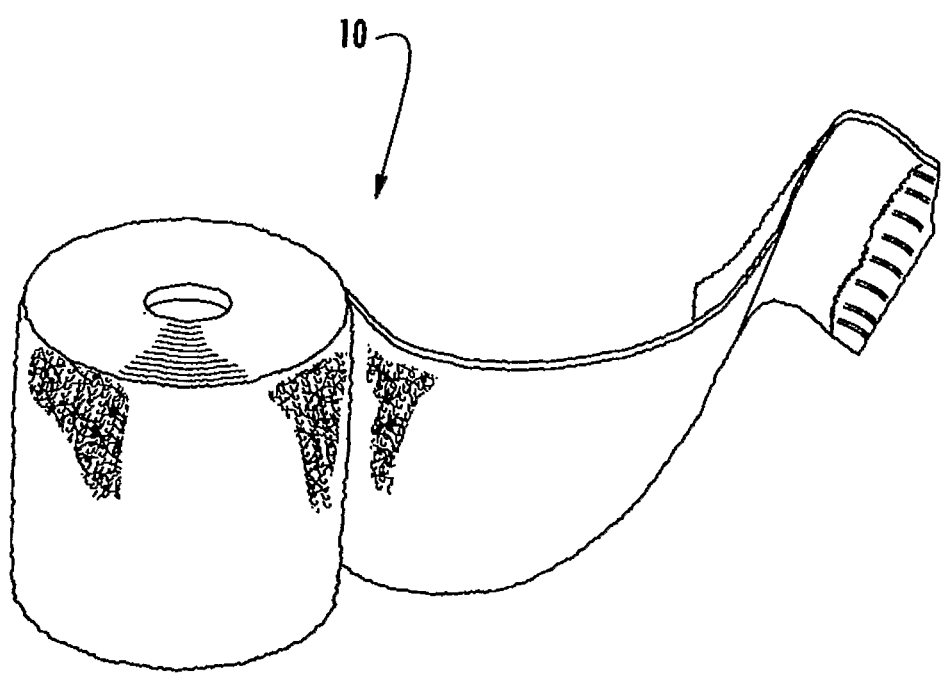
FIG. 1 is a perspective view of a continuous roll of the sleeve product.

Referring now specifically to the drawings, a water-resistant orthopedic undercast sleeve product according to the present invention is illustrated in FIG. 1 and shown generally at reference numeral 10. The particular embodiment shown in FIG. 1 is a roll-form product, and can be cut to length as needed. Indicia noting particular lengths can be placed on the product 10 to indicate where a cut may be made. The indicia may be a mark, a series of dropped stitches, or any other suitable manner of indicating a particular length.

Alternatively, the product 10 may be pre-cut into one or more lengths and packaged in that form, for example, in a bag or envelope from which a pre-cut length of product 10 is removed when needed.

Figure 2:
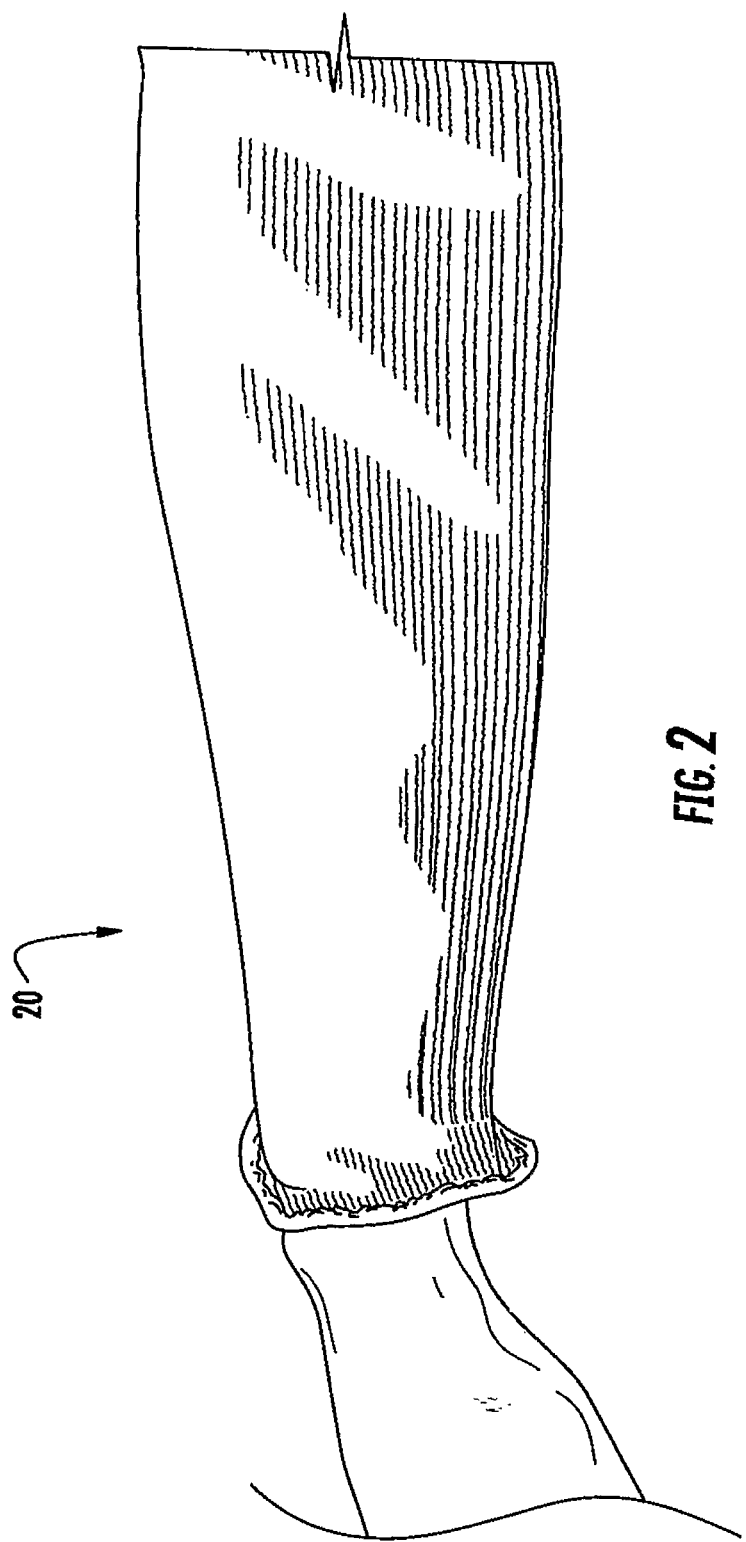
FIG. 2 is a perspective view of a sleeve in place on the forearm of a patient.

Referring now to FIG. 2, the sleeve product 10, whether originally in roll-form or pre-cut, is placed on a limb to form a water-resistant orthopedic undercast sleeve 20. The sleeve 20 can be constructed using suitable materials that provide adequate cushioning underneath a cast and are easy to mold around the injured limb, such as foam, knitted or stretch-woven textile substrate, polymeric film, plastic material or a combination of these. In a preferred embodiment shown in FIG. 2, the sleeve 20 is constructed of a suitable textile fabric, which can be constructed using any suitable organic or inorganic fiber or a blend of these. The sleeve 20 is preferably constructed using a low moisture regain, hydrophobic fiber such as polyester or polypropylene. The textile substrate can be either a single knit or a double knit construction.

In the most preferred form, the sleeve 20 is knitted using a hydrophobic fiber, such as polypropylene. The yarns selected for knitting the sleeve 20 can be a monofilament or a multifilament or a blend of both. In the preferred embodiment, the sleeve 20 is knitted using a hydrophobic, low filament, multifilament yarn with a filament count of at least 10 and having a total denier of between 50 and 2000, and preferably 500-1500.

The textile substrate can be knitted using any suitable knit structure and design, including but not limited to plain knit, rib knit, jersey knit, loop/terry knit and an interlock knit. In the most preferred form the sleeve 20 is knitted using a rib design such as 1×1, 2×1, 2×2 or 3×1 rib. A typical rib 2×2 rib knit pattern is shown in FIG. 2.

The water-resistant performance of the undercast sleeve 20 will depend on the type of fiber, yarn and fabric construction. Hence the sleeve 20 may or may not require further treatment or finishing to enhance its water resistance. For example, the sleeve 20 may be treated with a suitable fluorochemical or nano based water repellant coating or other waterproof/water-resistant coating techniques that improves or imparts a water-resistant characteristic to the sleeve 20.

Alternatively, the water-resistant sleeve 20 can be constructed using yarns with a water-resistant characteristic. Yarns having a water-resistant characteristic can be achieved by various methods, including but not limited to, incorporating a suitable filler, finish, or coating while extruding the filaments; coating the filaments with an appropriate finish during an extrusion/spinning process; or coating the filaments in a separate process. The yarns may be treated with a wax, silicone, fluorochemical product or coated with a nano-coating or any other suitable water-resistant product.

Figure 3:
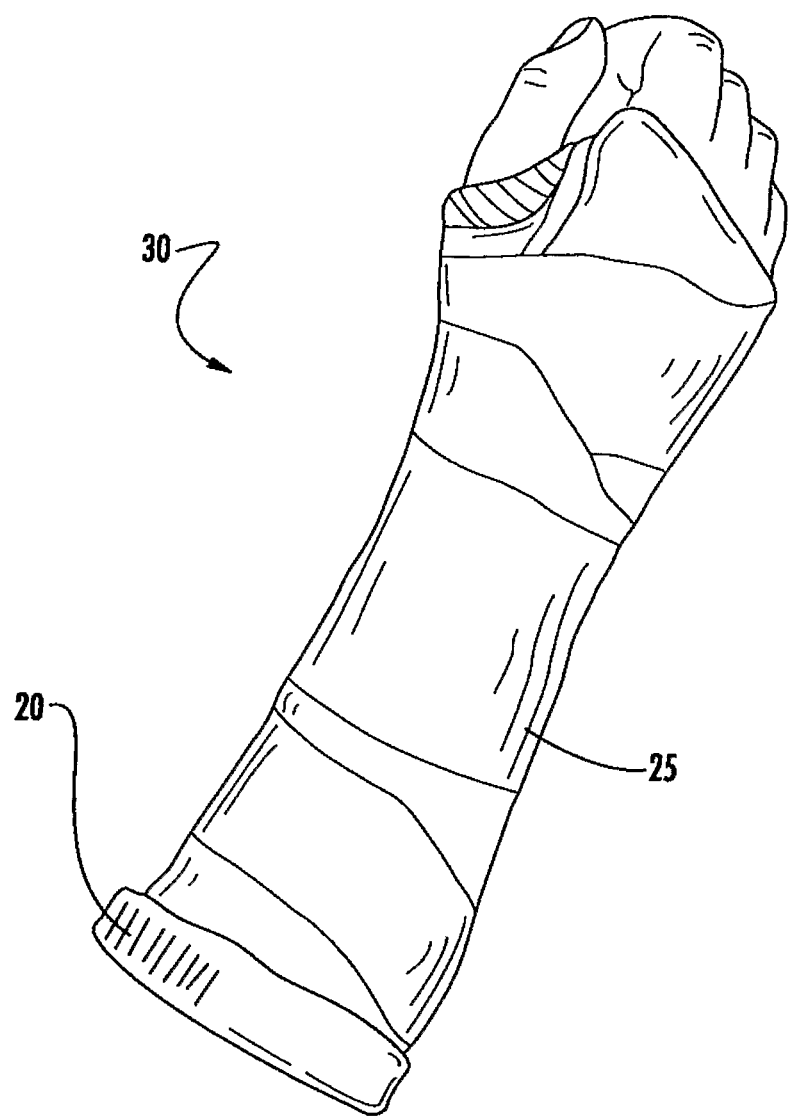
FIG. 3 is a perspective view of a cast in place on a limb, including the sleeve according to an embodiment of the invention.

As is shown in FIG. 3, the sleeve 20 resides against the skin and beneath an overlying wrapping of cast tape 25 to form a completed cast structure 30. As noted above, the sleeve 20 is intended to replace both the stockinette and padding of a conventional cast system. For this reason, the sleeve is constructed with a loft, bulk or thickness that provides adequate protection to the skin and bony prominences when applied under an orthopedic cast.

It has been observed during development that a sleeve with a hydrophobic performance will not function correctly without a means of conveying the moisture not only away from the skin, but out of the space between the sleeve 20 and cast tape 25. This is accomplished by, in the knitted embodiment, utilizing the rib knit to define egress channels between the ribs to convey moisture longitudinally along the length of the cast 30 to the surrounding air. Water movement and drying of the textile substrate is greatly improved by fewer yarn filaments and orientation, which can trap water molecules retaining a feeling of wetness in the area of the skin.

Alternatively, spacer fabrics may be suitable, with spaced-apart faces of the fabric defining an intermediate channel for transporting moisture away from both the sleeve and the cast tape. The spacer fabric is formed as or into a tube and has sufficient elasticity to form to the shape of the limb in the same manner as the sleeve 20 shown in FIG. 2.

Further alternatives may include open cell foam products in the form of sheets with channels or grooves molded or otherwise formed into the surface of the foam to serve as channels for transporting moisture away from the foam sleeve and the cast tape. The sheets are formed as or into tubes and have sufficient elasticity to form to the shape of the limb in the same manner as the sleeve 20 shown in FIG. 2.

The waterproof sleeve 20 may also be constructed using a tubular substrate with a top surface and a bottom surface and a series of interconnecting yarns between them. The top and bottom surface of the sleeve may also be joined by stitching, gluing, ultrasonic or other suitable means. The top and bottom surface can be knitted using the same or different structure and design.

A water-resistant undercast sleeve is described above. Various details of the invention may be changed without departing from its scope. Furthermore, the foregoing description of the preferred embodiments of the invention and the best mode for practicing the invention are provided for the purpose of illustration only and not for the purpose of limitation.

We claim:

1. A water-resistant orthopedic undercast sleeve, comprising:
    (a) a tubular sheet material formed of extruded filaments having water-resistant properties and a thickness sufficient to provide both cushioning and moisture transport in a single layer between a cast and a limb onto which the water-resistant orthopedic undercast sleeve is applied, the tubular sheet material comprising a three dimensional tubular knitted fabric constructed from separate, spaced-apart top and bottom layers wherein each of the layers is of knit construction and the layers are joined together by interconnecting yarns; and
    (b) moisture egress channels formed in the top and bottom layers by their knit construction and also formed between the top and bottom layers for transporting moisture away from the limb, longitudinally along the length of the water-resistant orthopedic undercast sleeve, and out of a space between the water-resistant orthopedic undercast sleeve and cast, the tubular sheet material having sufficient resistance to compression so as to maintain the moisture egress channels subsequent to application of the cast over the tubular sheet material;
    wherein the tubular sheet material comprises a water-resistant finish coating comprising a nano-coating;
    wherein the tubular knitted fabric is formed in an elongate roll of sufficient length to permit multiple lengths suitable for application to the limb to be severed from the elongate roll, as and when needed, and wherein a plurality of indicia noting particular lengths corresponding to the limb are located along the length of the tubular knitted fabric to indicate where a cut may be made;
    wherein the water-resistant orthopedic undercast sleeve is knitted from a hydrophobic, low filament, multifilament yarn with a filament count of at least 10 and having a total denier of between 500-1500;
    wherein the tubular knitted fabric is provided in pre-cut lengths suitable for application to a limb of a predetermined size and length; and
    wherein the tubular knitted fabric comprises low moisture regain hydrophobic fiber comprising polypropylene.

2. A water-resistant orthopedic undercast sleeve, comprising:
    (a) a tubular sheet material, formed of a low moisture regain hydrophobic polypropylene fiber, having a thickness sufficient to provide both cushioning and moisture transport in a single layer between a cast and a limb onto which the water-resistant orthopedic undercast sleeve is applied, the tubular sheet material comprising a three dimensional tubular knitted fabric having a nano-coating water-resistant finish and constructed from separate, spaced-apart top and bottom layers wherein each of the layers is of knit construction and the layers are joined together by interconnecting yarns;
    (b) moisture egress channels formed in the top and bottom layers by their knit construction and also formed between the top and bottom layers for transporting moisture away from the limb, longitudinally along the length of the water-resistant orthopedic undercast sleeve, and out of a space between the water-resistant orthopedic undercast sleeve and cast, the tubular sheet material having sufficient resistance to compression so as to maintain the moisture egress channels subsequent to application of the cast over the tubular sheet material; and
    (c) wherein the tubular knitted fabric is formed in an elongate roll of sufficient length to permit multiple lengths suitable for application to the limb to be severed from the elongate roll, as and when needed, and wherein a plurality of indicia noting particular lengths corresponding to the limb are located along the length of the tubular knitted fabric to indicate where a cut may be made; and
    wherein the water-resistant orthopedic undercast sleeve is knitted from a hydrophobic, low filament, multifilament yarn with a filament count of at least 10 and having a total denier of between 500-1500.

* * * * *